United States Patent [19]

Luomanen et al.

[11] 4,425,911

[45] Jan. 17, 1984

[54] BITE-BLOCK

[76] Inventors: Raymond Luomanen, 484 West Shore Trail, Sparta, N.J. 07871; Jack C. Luomanen, 1818 Acton St., Berkley, Calif. 94702

[21] Appl. No.: 287,057

[22] Filed: Jul. 27, 1981

[51] Int. Cl.³ ............................................. A61M 25/02
[52] U.S. Cl. ............................... 128/200.26; 128/136; 128/DIG. 26
[58] Field of Search ................... 128/200.26, 4, 10, 15, 128/207.14, 207.15, 207.17, DIG. 26, 136, 205.25, 207.18

[56] References Cited

U.S. PATENT DOCUMENTS

| | | | |
|---|---|---|---|
| 316,636 | 4/1895 | Miles | 128/136 |
| 2,693,182 | 11/1954 | Phillips | 128/207.14 |
| 2,820,457 | 1/1958 | Phillips | 128/207.14 |
| 2,857,911 | 10/1958 | Bennett | 128/207.14 |
| 2,908,269 | 10/1959 | Cheng | 128/207.17 |
| 3,090,122 | 5/1963 | Erickson | 32/33 |
| 3,139,088 | 6/1964 | Galleher, Jr. | 128/207.14 |
| 3,167,072 | 1/1965 | Stone et al. | 128/DIG. 26 |
| 3,496,936 | 2/1970 | Gones | 128/136 |
| 3,568,680 | 3/1971 | Raimo | 128/207.14 |
| 3,774,616 | 11/1973 | White et al. | 128/200.26 |
| 4,030,493 | 6/1977 | Walters et al. | 128/207.14 |
| 4,198,970 | 4/1980 | Luomanen | 128/207.15 |
| 4,256,099 | 3/1981 | Dryden | 128/207.15 |
| 4,326,515 | 4/1982 | Shaffer et al. | 128/DIG. 26 |

Primary Examiner—Henry J. Recla
Attorney, Agent, or Firm—Hubbell, Cohen, Stiefel & Gross

[57] ABSTRACT

A bite-block for intubated endoctracheal tubes and the like is disclosed. It includes a body (12) of substantially rectangular cross section, the body (12) having a central channel (18) open at the top and a pair of open side channels (20, 22) on either side of the central channel (18). A projection (16) conforming to the curve of Spee extends laterally from the body (12), the surfaces (32, 34) of the projection (16) being configured for engagement with teeth other than the incisors. A face plate (14) is secured to the anterior end of the body (12), and has apertures (24, 26, 28) communicating with the channels (18, 20, 22) for accommodating intubation of an endotracheal tube (44), suction catheter (46) or the like.

7 Claims, 4 Drawing Figures

BITE-BLOCK

TECHNICAL FIELD

This invention pertains to bite-blocks and more particularly to bite-blocks for patients with intubated endotracheal tubes, and requiring suction catheters and the like.

BACKGROUND ART

In my U.S. Pat. No. 4,198,970, the contents of which are hereby incorporated herein by reference in their entirety, I disclose an airway having a plurality of channels, one for supporting an endotracheal tube in the midline of the throat, and two others for supporting additional tubes for suctioning fluids from both the hypopharynx and the nasopharynx. The airway includes a straight section and an integral curved section, the latter serving to engage and hold down the patient's tongue to prevent the tongue from slipping into the patient's throat. While the airway disclosed in my prior patent is well suited for use with unconscious patients, it is preferably not used for patients recovering consciousness or in a semiconscious state. The reason is that patients emerging from unconsciousness begin to recover their laryngeal reflex which is responsible for the regurgitation of foreign matter from the throat. When an endotracheal tube is in place in a full airway such as that disclosed in my prior patent, the laryngeal reflex tends to regurgitate the lower, curved portion of the airway. Accordingly, when it is observed that a patient fitted with an endotracheal tube is regaining the laryngeal reflex, the airway is removed and a bite-block substituted. The primary difference between a bite-block and oral airway is that a bite-block does not include a portion extending into the throat for holding down the patient's tongue. Consequently, the bite-block, unlike a full airway, does not activate the laryngeal reflex.

The prior art discloses numerous bite-blocks for supporting an endotracheal tube. The simplest form is a rubber block having a central bore. The endotracheal tube is inserted through the bore and the block placed in the patient's mouth such that the patient bites on the block, and not on the tube. The rubber block may be provided with a circumferential groove for the front teeth. An example of such a prior art bite-block is disclosed in U.S. Pat. No. 316,636 issued to Miles, although the patent does not specifically disclose use of the bite-block for holding an intubated endotracheal tube. A similar arrangement particularly intended for receiving a drainage tube for use during dental operations is disclosed in U.S. Pat. No. 3,090,122 issued to Erickson. Essentially similar arrangements are also disclosed in U.S. Pat. Nos. 2,857,911 issued to Bennett, 3,139,088 issued to Galleher, and 4,030,493 issued to Walters et al.

U.S. Pat. No. 2,693,182 issued to Phillips discloses an arrangement essentially similar to those discussed above, except that means are provided for releasably securing the endotracheal tube against unintended axial movement. However, the means disclosed for effecting such securement is relatively complex. In Phillips' later issued U.S. Pat. No. 2,820,457, he discloses an essentially similar arrangement, but in addition provides a plurality of apertures in the face plate for accommodating the insertion of additional apparatus into the mouth. However, apart from the apertures in the face plate, the device does not include any means for positioning such additional apparatus in the mouth.

Like the later Phillips+ patent, U.S. Pat. No. 2,908,269 issued to Cheng discloses a bite-block including means for releasably securing the endotracheal tube against unintended axial displacement. The Cheng device also includes an additional aperture in the face plate for accommodating the insertion of a suction tube or the like. However, also like the Phillips' patent, the device disclosed by Cheng is disadvantageous in that the means for releasably securing the endotracheal tube is relatively complex, and means are not provided for positively positioning the suction tube in the mouth. Furthermore, the Cheng device is retained in place by a strap which extends about the patient's head and neck. Obviously, such strap contributes to patient discomfort.

A further disadvantage of all the prior art bite blocks discussed above is that they are retained in place by the clamping action of the front teeth. Inasmuch as many persons today have one or more caps on their front teeth, such clamping can cause damage to the caps. The advantage of this bite-block is that the biting force is on the posterior teeth, gaining further stabilization of the device in the patient's mouth without putting undue pressure on any existing anterior dental prostheses.

DISCLOSURE OF THE INVENTION

According to the present invention, I have developed a simple, anatomically compatible bite-block capable of simultaneously accommodating an intubated endotracheal tube as well as two suction catheters. The bite-block of the invention includes means for securing the endotracheal tube against axial displacement, and also includes means for positively positioning the suction tubes in the patient's mouth and pharynx. Additionally, it is held in place other than by the incisors, thereby avoiding possible damage to capped front teeth.

The preferred bite-block in accordance with the invention comprises a body having a substantially rectangular cross section. The body is provided with a continuous, U-shaped central channel having an open top, and a pair of open sided U-shaped channels on either side of the central channel. A projection extends laterally from one side of the body, the projection having upper and lower surfaces which are configured for engagement with other than the incisors. The projection is curved to conform with the curve of Spee thereby rendering the bite-block anatomically compatible, and the spacing between the upper and lower surfaces of the projection is such that when the bite-block is in place, contact between the incisors and the bite-block is precluded. A face plate secured to the anterior end of the body engages the patient's mouth for preventing inward displacement of the bite-block. The face plate is provided with apertures communicating with the central and side channels. The face plate can be used to tape the bite-block to the patient's chin for stability when the patient is moved.

In use, the endotracheal tube is disposed in the central channel, and the side channels are used for inserting suction catheters or other instruments. Because the side channels extend the length of the bite-block, they guide the suction catheters into the patient's pharynx thereby facilitating effective suctioning. The preferred bite-block includes a plurality of openings extending between the central channel and each of the side channels. By disposing one or both of the suction catheters in the side channels such that their distal ends are in the vicinity of these openings, suctioning of fluids accumulating between the endotracheal tube and the walls defining the central channel may be effected.

The bite-block preferably includes two pairs of confronting tapered ribs extending into the central channel. The space between each pair of ribs is slightly less than the diameter of the endotracheal tube whereby the ribs frictionally engage the tube for precluding unintended axial movement thereof. The central channel is preferably rounded for securely seating the endotracheal tube. Also, the laterally extending projection preferably includes a flange on the portion thereof remote from the body of the bite-block. The flange is dimensioned for seating between the teeth and cheek and prevents lateral movement of the bite-block in the mouth.

Further features and advantages of the bite block according to the present invention will be more fully apparent from the following detailed description and annexed drawings of the presently preferred embodiment thereof.

BEST MODE FOR CARRYING OUT THE INVENTION

Figure 1:
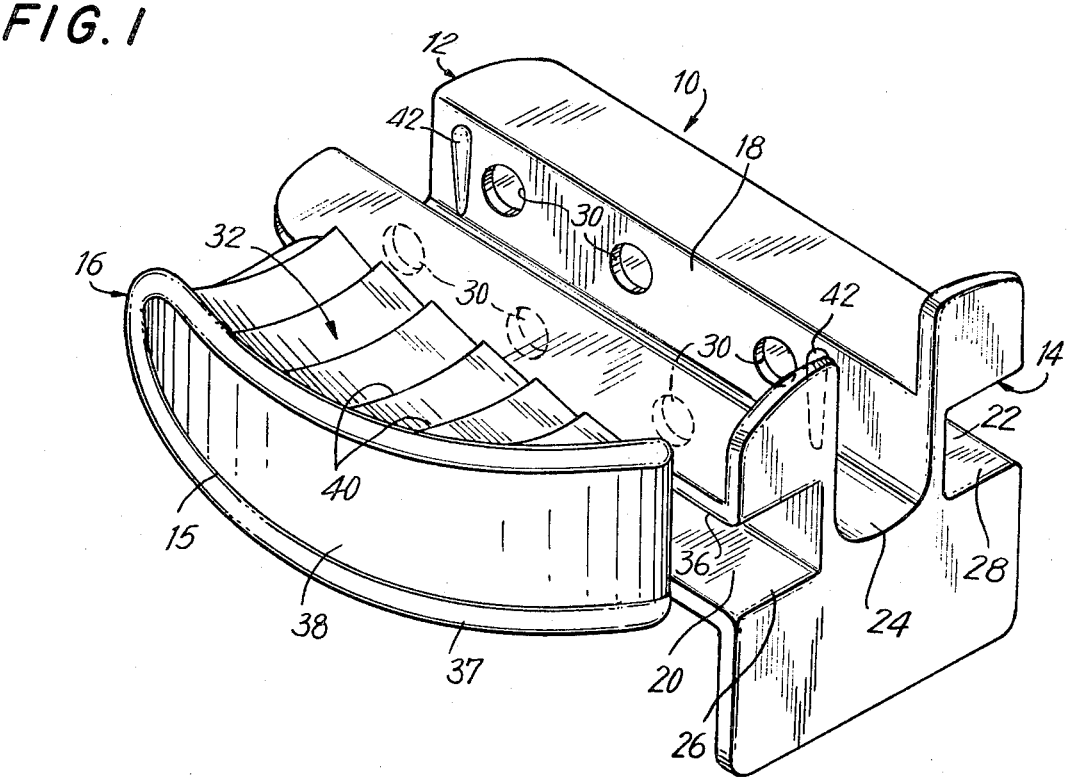
FIG. 1 is a perspective view of the preferred bite-block in accordance with the present invention showing the top, one side, and the anterior end thereof.
Figure 2:
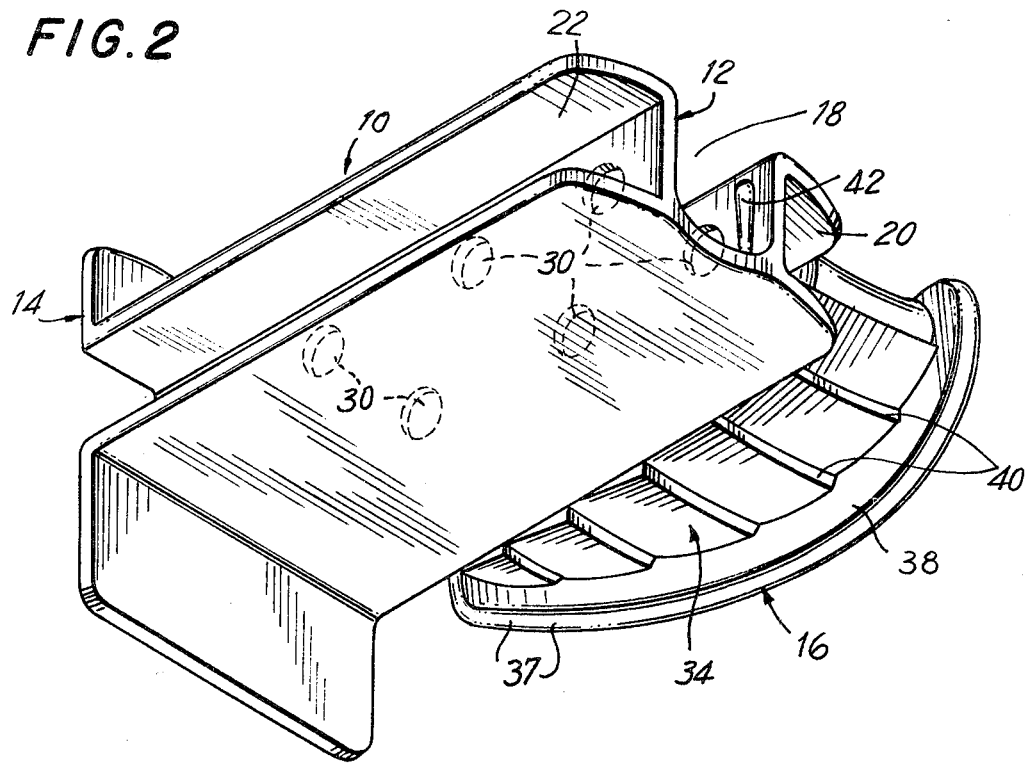
FIG. 2 is another perspective view of the preferred bite-block showing the bottom, the other side, and the posterior end thereof.

Referring now to the drawings, and initially to FIGS. 1–2 thereof, the preferred bite-block in accordance with the present invention is generally designated by the reference numeral 10. As illustrated, the bite-block 10 includes a body 12 having a substantially rectangular cross section, a face plate 14 joined to the body 12 at the anterior end thereof, and a projection 16 extending laterally from the body 12 on one side thereof.

The body 12 is provided with a preferably continuous longitudinally extending centrally located U-shaped channel 18 open at the top, and a pair of preferably continuously extending open-sided U-shaped channels 20 and 22 on either side of the channel 18. The face plate 14 is provided with apertures 24, 26 and 28 communicating with channels 18, 20 and 22, respectively, for accommodating intubation as will be more fully described hereinafter. As preferred and best shown, a plurality of spaced openings 30, preferably three in number, extend between the central channel 18 and each of the side channels 20, 22. The reason for this will be more fully explained hereinafter.

Figure 3:
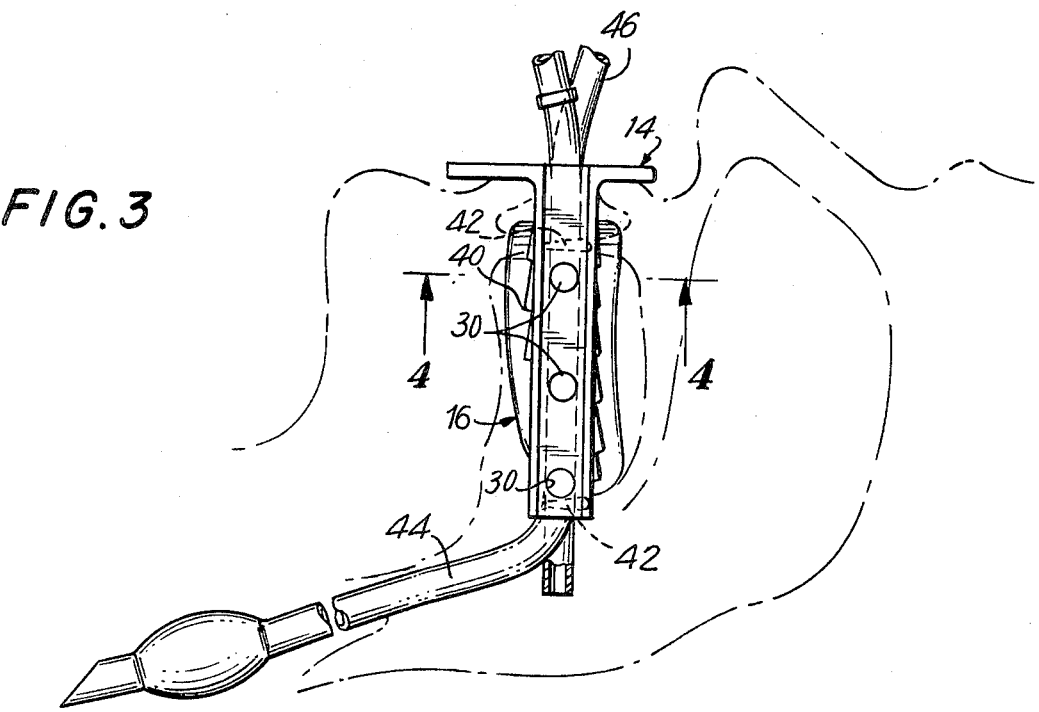
FIG. 3 is a side elevation showing the preferred bite-block in situ.

As best shown in FIGS. 1-3, the upper and lower surfaces 32, 34 of the projection 16 extend substantially perpendicular to the side 36 of the body 12. The projection 16 terminates in a flange 38 substantially parallel to the side 36, the flange 38 extending above and below the surfaces 32, 34, respectively. Ridges or steps 40 are provided on the upper and lower surfaces 32, 34, the ridges 40 being configured for complementary engagement with the patient's canines, bicuspids, and molars. As illustrated, the surfaces 32, 34, as well as the peripheral surface 37 of the flange 38, are preferably curved to conform with the curve of Spee, the anatomical term given to the natural curvature of the dental ridges.

Figure 4:
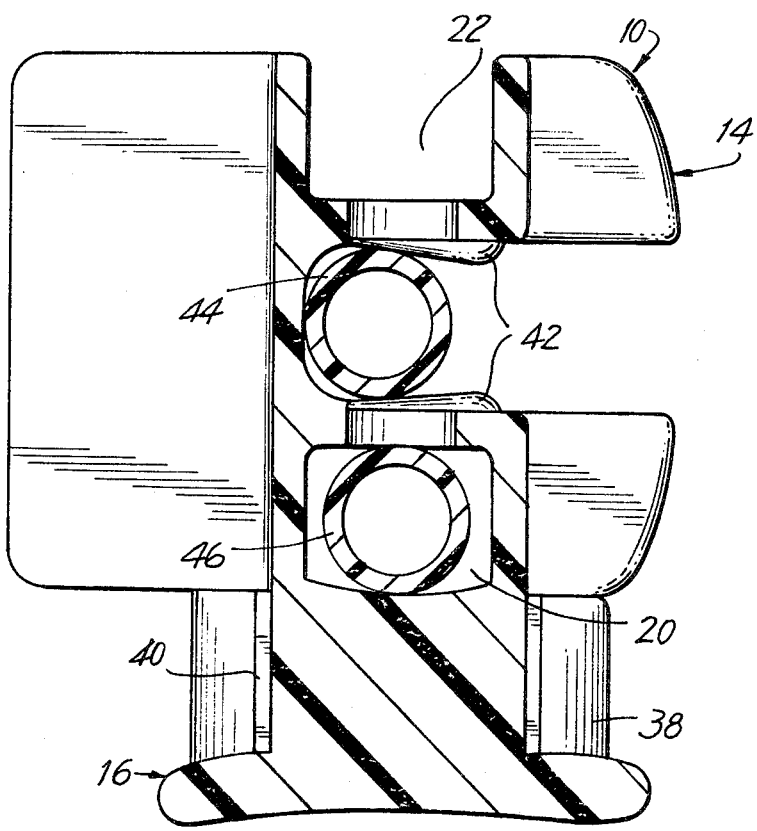
FIG. 4 is a vertical section take substantially along the line 4—4 in FIG. 3.

As preferred and best shown in FIGS. 1, 2 and 4, two spaced pairs of ribs 42 extend into the channel 18. As illustrated, the ribs 42 are tapered such that they gradually increase in thickness from the bottom of the channel 18 to their point of termination at substantially the top of the channel. The reason for this is explained below.

Those skilled in the art will appreciate that the bite-block 10 may be constructed from a variety of different materials and in a variety of different ways, all of which are acceptable for purposes of the present invention. For example, if a reuseable bite-block is contemplated, the bite-block will preferably be comprised of a suitable metal, such as aluminum, or a metal alloy. On the other hand, if, as is presently preferred, it is intended that the bite-block 10 be expendable, it is preferably injection molded from rubber or plastic. For example, a medical grade, non-allergenic ethylene vinyl acetate or polyethylene plastic may be used. Although not absolutely necessary, an integral construction is preferred. Whatever method of construction is employed, it is desirable that the edges of the bite-block 10 be rounded and all surfaces be smoothed to avoid discomfort and possible damage upon insertion. It is presently contemplated that the actual dimensions of the bite-block 10 will vary to accommodate use with children and adults of varying sizes. Also, since some persons require larger endotracheal tubes than others, it is contemplated that some versions may have a wider central channel and shallower side channels than others.

With particular reference now to FIGS. 3 and 4, in use, the bite-block 10 will generally be employed to secure an already intubated endotracheal tube 44 in place. For example, the endotracheal tube 44 may originally have been in place in an airway such as that disclosed in my prior U.S. Pat. No. 4,198,970, the airway being removed when the laryngeal reflex returns as the patient regains consciousness. Assuming that the endotracheal tube 44 is already in place, the bite-block 10 is inserted into the patient's mouth and the tube 44 seated in the channel 18. As shown, the width of the channel 18 is preferably slightly wider than the diameter of the tube 44. The spacing between the inwardly projecting ribs 42 is, however, preferably slightly less than the diameter of the tube 44. Accordingly, once the tube 44 is pressed downward into the preferably rounded bottom of the channel 18 to the position shown in FIG. 4, the ribs 42 will frictionally engage the tube thereby preventing unintended axial movement thereof. As shown in FIG. 3, when the bite-block 10 is in place, the plate 14 engages the patient's upper and lower lips for preventing accidental inward displacement of the bite block into the patient's mouth.

Focusing now on the projection 16, when the bite-block 10 is in place, the upper and lower surfaces 32, 34 of the projection 16 engage the confronting surfaces of the patient's canines, bicuspids, and molars. Because the surfaces 32, 34 are formed to conform with the curve of Spee, all of the aforementioned teeth engage the surfaces 32, 34, thereby creating a comfortable fit. Anatomical compatibility is further enhanced by the ridges 40 on the surfaces 32, 34 which are angled to complement the engaging surfaces of the teeth.

Because of the spacing between the surfaces 32 and 34, when the patient's canines, bicuspids, and molars engage the projection 16, the incisors, which extend into the space between the projection 16 and face plate 14, are held in spaced relation from the body 12. While the incisors are not completely out of contact with the body of the airway, they do not comprise the focus of the clamping action of the teeth. Also, by sight, the disastama between the two central incisors provides a mechanism to further check the mid-line position of the device. Inadvertent side to side displacement of the bite-block 10 in the patient's mouth is avoided by the flange 38 which seats in the space between the patient's teeth and cheek.

The projection 16 is preferably of sufficient length such that the surfaces 32, 34 engage all of the upper and lower canines, bicuspids, and molars on one side of the patient's mouth. However, from this description, those skilled in the art will appreciate that the bite-block 10 would function with substantially equal effectiveness if the surfaces 32, 34 engaged, for example, only the bicuspids and molars, or even only the molars. Further, while a projection 16 is preferred and shown on only one side of the bite-block 10, this is not absolutely necessary, and a corresponding projection 16 could be formed on the other side of the bite-block 10 as well.

Focusing attention now on the channels 20, 22 and the openings 30, use of an endotracheal tube is commonly accompanied by the accumulation of phlegm, saliva or even blood in the patient's pharynx. Some of this accumulation may be sucked up into the space between the walls of the channel 18 and the endotracheal tube 44. Accordingly, it is desirable to provide means to suction such fluids. As will be apparent immediately hereinafter, such suctioning is readily accommodated by the bite-block 10.

Thus, as best shown in FIG. 3, suctioning of the pharynx may be effected by intubating a suction catheter 46 through the aperture 26 in the face plate 14 and into the channel 20. The channel 20 guides the catheter 46 to the patient's pharynx whereupon fluids accumulated therein may be effectively suctioned. If desired, an additional suction catheter may be guided through the opening 28 in the face plate 14 and into the other side channel 22. To suction fluids accumulating between the walls of the channel 18 and the tube 44, the suction catheter 46 is partially intubated in one of the channels 20, 22 such that its distal end is in the vicinity of the openings 30. When this is done, it will be apparent that suctioning will withdraw fluids accumulated in the channel 18 through the openings 30. It is also contemplated that the channels 20, 22 may be used for intubating other instruments. Additionally, the bite-block 10 may be used for such procedures as flexible bronchoscopy. In such event, the bronchoscope will be inserted in the endotracheal tube 44, and like the tube will be maintained in the midline of the patient's throat. Since the bronchoscope is of lesser diameter than the endotracheal tube 44, the patient can breathe through the unobstructed portion of the tube 44 thus allowing suctioning through the channels 20, 22 as is more fully described above.

Removal of the bite-block 10 is easily accomplished by first removing any instruments in the channels 20, 22 and then pushing the endotracheal tube 44 upward until it is above the ribs 42. The bite-block 10 may then be removed, followed by extubation of the endotracheal tube 44.

It will be apparent from the foregoing description that the bite-block 10 of the present invention is capable of firmly positioning an endotracheal tube while at the same time accommodating suctioning of accumulated fluids. In addition, because the bite-block 10 is held in place in the mouth by the rear teeth, and not the incisors, possible damage to caps on the incisors is avoided.

Moreover, the bite-block 10 is simple, anatomically compatible, relatively inexpensive, and suitable for integral construction as, for example, by injection molding from plastic.

While I have herein shown and described the preferred bite-block in accordance with the present invention and have suggested certain modifications thereto, it will be apparent to those skilled in the art that still further changes and modifications may be made therein without departing from the spirit and scope of the invention. For example, while the face plate 14 illustrated in the drawings is preferred, other face plate designs and constructions are acceptable. Accordingly, the above description should be construed as illustrative and not in a limiting sense, the scope of the invention being defined by the following claims.

We claim:

1. A bite-block for use by a human subject comprising:
    a body having a substantially rectangular cross section having an anterior end and a posterior end, said body including a U-shaped central channel having an open top, and a pair of open-sided U-shaped channels on either side of said central channel;
    a transverse plate secured to the anterior end of said body, said plate being engageable over the mouth of said subject and having apertures communicating with said channels; and
    a projection secured to one side of said body and extending laterally therefrom from a point spaced from said plate to a point near the posterior end thereof, said projection extending laterally sufficiently such that said body is disposed substantially centrally of the mouth and said projection is disposed between upper and lower teeth other than the incisors when the bite-block is disposed in the mouth, said projection including upper and lower surfaces conforming to the curve of Spee, said upper surface being configured for engagement with said upper teeth other than the incisors and said lower surface being configured for engagement with said lower teeth other than the incisors, said upper and lower surfaces being sufficiently spaced apart to preclude clamping of the incisors on said body when said upper and lower teeth other than the incisors engage, respectively, the upper and lower surfaces of the projection.

2. The bite-block according to claim 1, wherein said projection further comprises a flange on the side thereof remote from said body, said flange being dimensioned for seating between the teeth and the cheek.

3. The bite-block according to claim 2, wherein said projection extends from substantially the posterior end of said body to a point in spaced relation from said plate, wherein said teeth other than the incisors are the canines, bicuspids, and molars; and wherein said upper and lower surfaces are complementary to the engaging surfaces of said canines, bicuspids, and molars.

4. The bite-block according to claim 1 or 3, further comprising a pair of confronting ribs in said central channel for frictionally retaining a tube therein.

5. The bite-block according to claim 4, further comprising an opening extending between said central channel and each of said side channels.

6. The bite-block according to claim 1, further comprising an opening extending between said central channel and each of said side channels.

7. The bite-block according to claim 5, wherein said body, said projection, and said plate are integral.

* * * * *